US007957794B2

(12) United States Patent
Hochman et al.

(10) Patent No.: US 7,957,794 B2
(45) Date of Patent: Jun. 7, 2011

(54) SYSTEM AND METHOD FOR TRANSDUCING, SENSING, OR AFFECTING VAGINAL OR BODY CONDITIONS, AND/OR STIMULATING PERINEAL MUSCULATURE AND NERVES USING 2-WAY WIRELESS COMMUNICATIONS

(75) Inventors: Joel S. Hochman, Houston, TX (US); George Sarkis, Orinda, CA (US)

(73) Assignee: Athena Feminine Technology, Orinda, CA (US)

( * ) Notice: Subject to any disclaimer, the term of this patent is extended or adjusted under 35 U.S.C. 154(b) by 0 days.

(21) Appl. No.: 12/542,511

(22) Filed: Aug. 17, 2009

(65) Prior Publication Data

US 2010/0004707 A1    Jan. 7, 2010

Related U.S. Application Data

(62) Division of application No. 10/007,393, filed on Oct. 26, 2001, now Pat. No. 7,577,476.

(51) Int. Cl.
| | |
|---|---|
| A61B 5/04 | (2006.01) |
| A61B 5/05 | (2006.01) |
| A61B 5/00 | (2006.01) |
| A61B 10/00 | (2006.01) |
| A61B 5/103 | (2006.01) |
| A61B 5/117 | (2006.01) |

(52) U.S. Cl. ........ 600/546; 600/547; 600/549; 600/551; 600/587; 600/591

(58) Field of Classification Search .................. 600/300, 600/301, 304, 372, 373, 547, 549, 551, 573, 600/587, 591, 29, 38, 33; 607/39, 40, 41
See application file for complete search history.

(56) References Cited

U.S. PATENT DOCUMENTS

| | | | |
|---|---|---|---|
| 4,515,167 A | 5/1985 | Hochman | |
| 4,676,254 A | 6/1987 | Frohn | |
| 4,753,247 A | 6/1988 | Kirsner | |

(Continued)

FOREIGN PATENT DOCUMENTS

DE     2941363     4/1981

(Continued)

OTHER PUBLICATIONS

Vaginal Temperature Sensing Using UHF Radio Telemetry, McCreesh et al Med, Eng. Phys. vol. 18, No. 2, pp. 110-114 (1996).

(Continued)

*Primary Examiner* — Jeffrey G Hoekstra
(74) *Attorney, Agent, or Firm* — Robert W. Becker; Robert W. Becker & Assoc.

(57) ABSTRACT

A system for sensing vaginal conditions or for affecting vaginal or body conditions in a mammal. The system includes a portable probe unit and a separate controller unit, both of which include two-way communication devices to both transmit signals to, and receive signals from, each other, wirelessly and in real time. The substantially smooth and sealed outer surface of the cylindrical body of the probe unit has a rounded end and is dimensioned to permit comfortable and repeated insertion into, removal from, and containment entirely within a mammal's vagina. The probe body has a device substantially flush with its outer surface and configured to deliver electrical pulses, receive electrical pulses, sense or sample vaginal conditions and/or deliver medication. Signals to the probe unit comprise control and programming signals acting as a feedback loop configured to start, stop and/or alter activity of the substantially flush device of the probe unit, either automatically or manually, for sensing vaginal conditions or for affecting vaginal or body conditions.

20 Claims, 5 Drawing Sheets

U.S. PATENT DOCUMENTS

| | | |
|---|---|---|
| 4,844,076 A | 7/1989 | Lesho et al. |
| 5,209,238 A | 5/1993 | Sundhar |
| D393,311 S | 4/1998 | Kirsner |
| 5,916,173 A | 6/1999 | Kirsner |
| 6,080,118 A | 6/2000 | Blythe |
| 6,169,914 B1 | 1/2001 | Hovland et al. |
| 6,402,683 B1 | 6/2002 | Marty |
| 6,432,037 B1 | 8/2002 | Eini et al. |
| 6,453,199 B1 | 9/2002 | Kobozev |
| 6,860,859 B2 | 3/2005 | Mehrotra et al. |
| 2002/0010390 A1 | 1/2002 | Guice et al. |

FOREIGN PATENT DOCUMENTS

| | | |
|---|---|---|
| EP | 0040077 | 11/1981 |
| FR | 2709422 | 3/1995 |
| JP | 01107745 | 4/1989 |
| JP | 07313537 | 5/1995 |
| WO | WO 00/23030 | 4/2000 |

OTHER PUBLICATIONS

Vaginal Temperature Sensing Using UHF Radio Telemetry, McCreesh et al Med, Eng. Phys. vol. 18, No. 2, pp. 110-114 (1996).

FIG 1
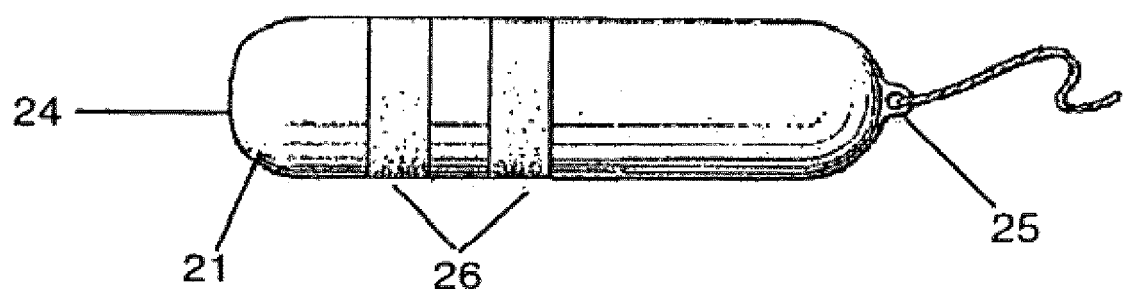
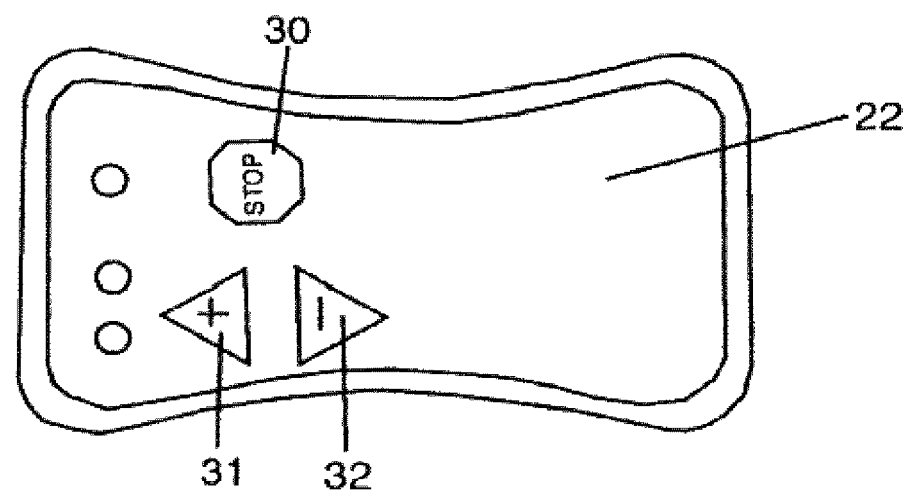
FIG 2

SYSTEM AND METHOD FOR TRANSDUCING, SENSING, OR AFFECTING VAGINAL OR BODY CONDITIONS, AND/OR STIMULATING PERINEAL MUSCULATURE AND NERVES USING 2-WAY WIRELESS COMMUNICATIONS

CROSS-REFERENCE TO RELATED APPLICATIONS

This application is a divisional application of Ser. No. 10/007,393 filed Oct. 26, 2001.

BACKGROUND OF THE INVENTION

The present invention relates to a system for transducing vaginal conditions, affecting vaginal or body conditions and/or stimulating perineal musculature and nerves. The present invention also relates to a method for accomplishing these functions.

U.S. Pat. No. 4,515,167, Hochman, discloses a self-contained stimulation device that was programmable, prior to use, using control buttons on the surface of the device itself. Signals could also be emitted from the device to an external unit for processing. The drawbacks of this known device include the inability to alter its operation during use. In addition, this known device is not very ergonomic due in particular to the surface control buttons that are necessarily present on the device for its programming and operation.

Other vaginally insertable probes are also known, such as the fertility probes of U.S. design Pat. No. 393,311 and U.S. Pat. No. 5,916,173, both to Kirsner. U.S. Pat. No. 4,753,247, Kirsner, discloses a probe that is connected by wires to an external housing containing batteries and electronic circuitry.

Prior known devices fail to provide a system that can provide stimulation, deliver medication, and/or obtain physiological data intravaginally, via a wireless 2-way communication and in real time.

It is therefore an object of the present invention to provide an ergonomic system and method that will allow, in a wireless manner and in real time, the transducing of vaginal conditions, the affecting of vaginal or body conditions, and the stimulation of perineal musculature and nerves in the human or other mammalian vagina, and in particular allows for real time remote control and/or programming of the intravaginally contained probe/transceiver unit.

BRIEF DESCRIPTION OF THE DRAWINGS

This object, and other objects and advantages of the present invention, will appear more clearly from the following specification in conjunction with the accompanying schematic drawings, in which:

FIGS. 1 and 2 show the probe/transceiver and the controller/transceiver units respectively of the system of the present invention;

SUMMARY OF THE INVENTION

Figure 3:
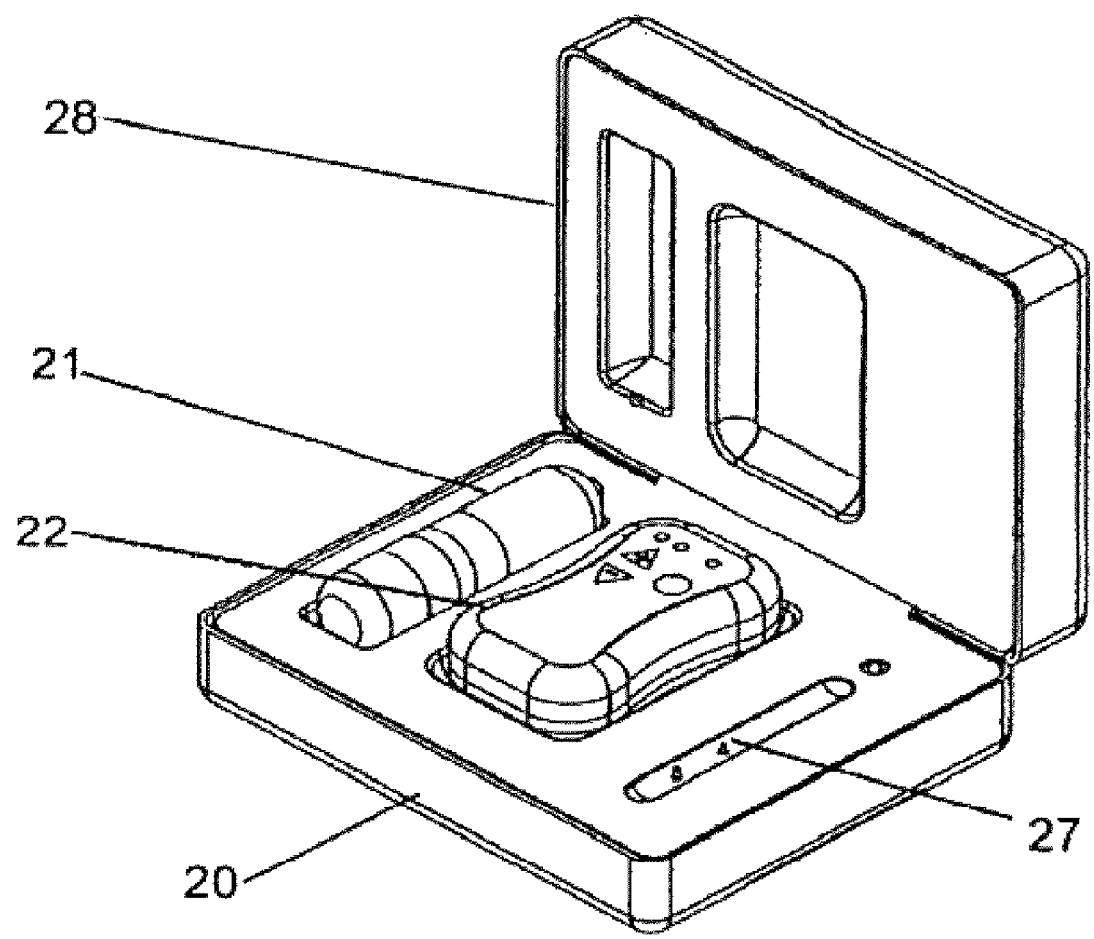
FIG. 3 shows the probe and controller units in a case.

The system of the present invention comprises: a separate, portable, non-implanted, intravaginally containable (i.e. in situ yet removable) combination probe and transceiver that is provided with means for sensing vaginal conditions, delivering signals or medication, and/or stimulating perineal musculature and nerves, wherein such probe unit is provided with 2-way wireless real time communication means for transmitting information that is transduced and for receiving control and programming signals; and a separate combination controller and transceiver that is provided with wireless means for sending signals to the probe unit and for receiving signals therefrom, wherein a wireless signal feedback loop is provided between the controller and probe units and external devices, networks and databases.

The combination probe and transceiver is, in particular, a pre-programmed unit. The programming of this unit can, however, be altered. As indicated, 2-way communication is provided between the probe unit and the controller unit, which can be a hand-held unit, but could alternatively or in addition be a PC or other similar computer unit.

The probe of the inventive system contains no wires or similar external means or surface controls, and is therefore comfortable to use.

When the probe unit of the inventive system is used as a stimulation unit, women are provided a safe, easy and convenient way to strengthen and tone their pelvic muscles without professional intervention or special training.

In addition, or alternatively, the probe unit of the inventive system can be provided with solid state transducers or other sensor means that would be able to identify, for example, sexually transmitted pathogens, cancerous changes in the cervix and vaginal environment, metabolic abnormalities, physiological markers of the fertility cycle, and other physiological information. It may also be possible in this way to identify diseases by DNA sequences or by disease-specific molecular odors. The inventive system thus affords the ability of being able to provide the earliest possible diagnosis and treatment of pathological conditions, since it is now possible with the inventive system to obtain intracorporeal physiological information without the need for parenteral or invasive sampling. In other words, physiological information can be wirelessly tracked and monitored, allowing observation and supervision of metabolic and fertility activities, among others. This can even be done from a remote site, since the diagnostic data can be wirelessly transmitted to local hubs, local area networks, personal computers, and the internet. Thus, the inventive system can provide sophisticated diagnostic data to the user, to her physician, and to internet-hosted diagnostic services. Of particular significance is that this transfer of information is accomplished in real time.

Further specific features of the present invention will be explained in detail subsequently.

DESCRIPTION OF PREFERRED EMBODIMENTS

Referring now to the drawings in detail, the inventive system, which is designated generally by the reference numeral 20 (FIG. 3), essentially comprises two separate straightforward, self-contained units, namely a combination probe and transceiver 21 and a combination controller and transceiver 22. The required components of these units are integrated and, where appropriate, sealed into these two units. The bodies of the units 21,22 are made of a plastic, such as those approved for medical use by the Food and Drug Administration. An example of such a plastic is medical grade level polycarbonate.

Although, as indicated previously, the inventive system 20 has numerous applications, including sensing or transducing vaginal conditions, affecting vaginal or body conditions, and/ or stimulating perineal musculature and nerves, the system will now be explained in conjunction with use as a stimulation system.

When the system 20 is used as a stimulation system, the combination probe and transceiver unit is characterized as a stimulator unit. In one specific embodiment of the present invention, such a stimulator unit is less than 1 inch in diameter and less than 4 inches in length. The end 24 of the unit 21 is rounded to facilitate vaginal insertion. The opposite end of the unit can be provided with, for example, an eyelet 25 to which a cord or similar device can be attached to facilitate removal of the reusable unit. The body of the unit is provided with at least one electrode ring 26 (two such rings are shown in the embodiment illustrated in FIG. 1), with these electrode rings being flush with the outer surface of the unit. The electrode rings 26 are designed to deliver electrical pulses to the muscles and/or nerves of the pelvic floor, and are preferably metallic rings, although they could also be made of non-metallic conducting material such as doped silicon. The stimulator unit 21 is furthermore provided with a microprocessor, a radio transmitter and a receiver mounted on a circuit board, an antenna and a sealed battery, as will be discussed in detail subsequently.

The operation of the combination probe and transceiver in its function as a stimulator unit will now be described by way of example. To begin a session, a woman would remove the hand-held combination controller and transceiver (the control unit) 22 and the stimulator unit 21 from the holder or case 28 (see FIG. 3), which also includes a tester 27 for the probe or stimulator unit. The stimulator unit 21 is then inserted into the vagina. The stimulator unit 21 can be turned on automatically at a low level when it is removed from the case 28; this can be accomplished, for example, either by a signal from the control unit 22 or can be triggered by a non-illustrated magnet located in the case 28. Although automatic powering up is preferred, the stimulator unit 21 can also be turned on manually using the on/off button 30 of the control unit 22.

The stimulator unit 21 can operate entirely automatically by being preprogrammed. For example, the unit can start at a low level of about 2 volts, can hold this voltage for approximately 30 seconds or any other desired period of time, and can then automatically ramp up to, for example, 5 volts. The stimulator unit 21 could also be operated manually by the control unit 22, or the control unit could be used to override the programmed stimulator unit 21. For example, the hand-held control unit 22 can be used to increase the stimulation strength in small steps until a user feels the muscles contract. This would be accomplished by using the Increase button 31. Should the woman feel any discomfort, she can decrease the strength of stimulation by pushing the Decrease button 32, or can turn the system off by pushing the OFF button 30. The system can be programmed to run for a specified period of time, for example in fifteen minute cycles, after which it will automatically shut off. The stimulator unit 21 can then be removed.

During a session, which, as indicated above, could run for approximately 15 minutes, the stimulator unit 21 is programmed to follow a pattern of several stimulation cycles, each of which is followed by a rest period with a repeat of the set of stimulation cycles and rest periods. The stimulation patterns are the well known Kegel patterns. The stimulator unit 21 can be programmed so that it will automatically ramp up to the setting of a previous use; in other words, the stimulator unit and/or the control unit 22 is provided with a memory.

Figure 4:
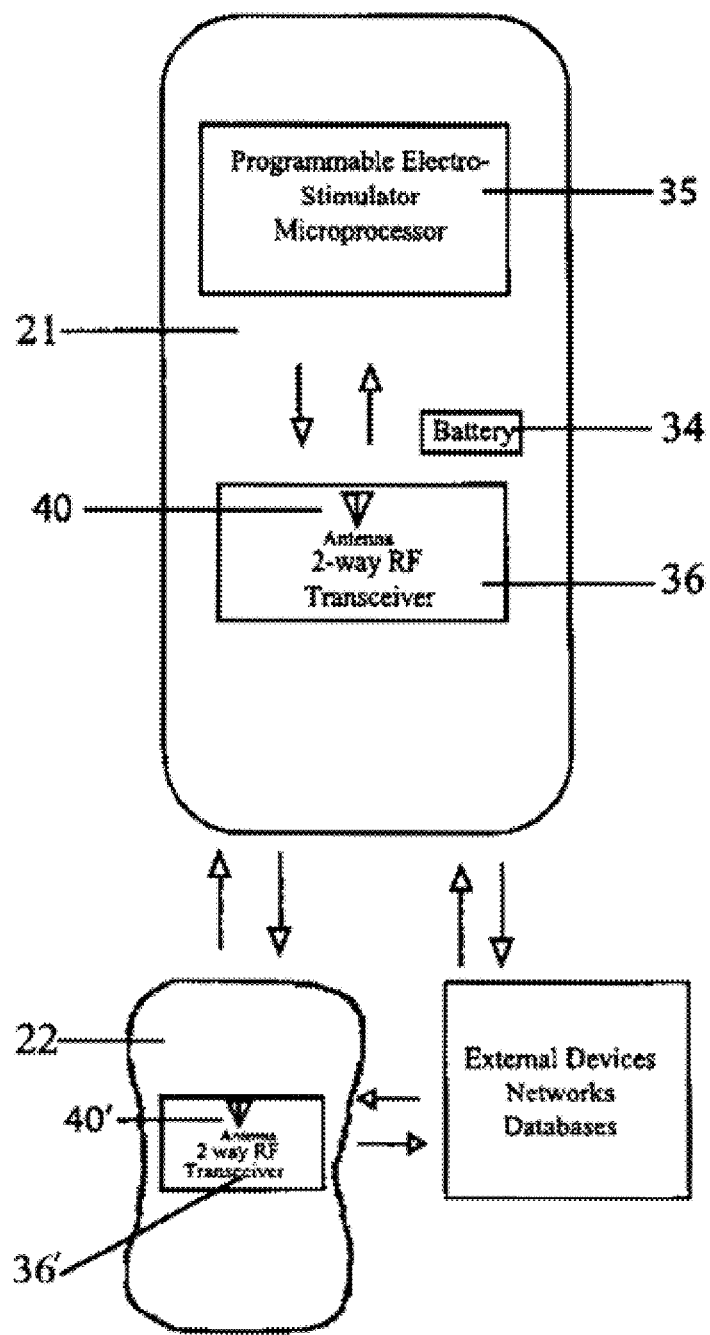
FIGS. 4-6 diagrammatically show the micro circuitry for various exemplary embodiments of the inventive probe and controller units.

To accomplish the various functions of the system 20, namely of the control unit 22 and the stimulator or combination probe and transceiver unit 21, these units are provided with a number of components (see FIG. 4). In particular, the stimulator unit 21 and control unit 22 respectively include a battery 34, a microprocessor 35, and a radio transmitter and receiver, or preferably a transceiver 36, 36' which includes an antenna 40, 40'. The radio transmitters and receivers, or transceivers, of the control unit 22 and of the probe unit 21 are miniature radio transceivers of the same low power class as of the known remote keyless locking devices used in automobiles. The programmable microprocessors of the units are designed to receive signals from the other unit and to deliver signals thereto, all in a wireless signal feedback loop, which may be closed or interactive. By way of example, electrical stimulation pulses can be delivered to the perineal musculature via the aforementioned electrode rings 26.

The control unit 22 and the probe unit 21 can also be provided with wireless means to transmit signals to or receive signals from external devices, networks or databases, including a PC which may be located in a doctor's office, thereby facilitating data transmission and analysis.

It should also be noted that although the control unit 22 is preferably a hand-held unit, it could also be an appropriately programmed and equipped PC or the like.

Figure 5:
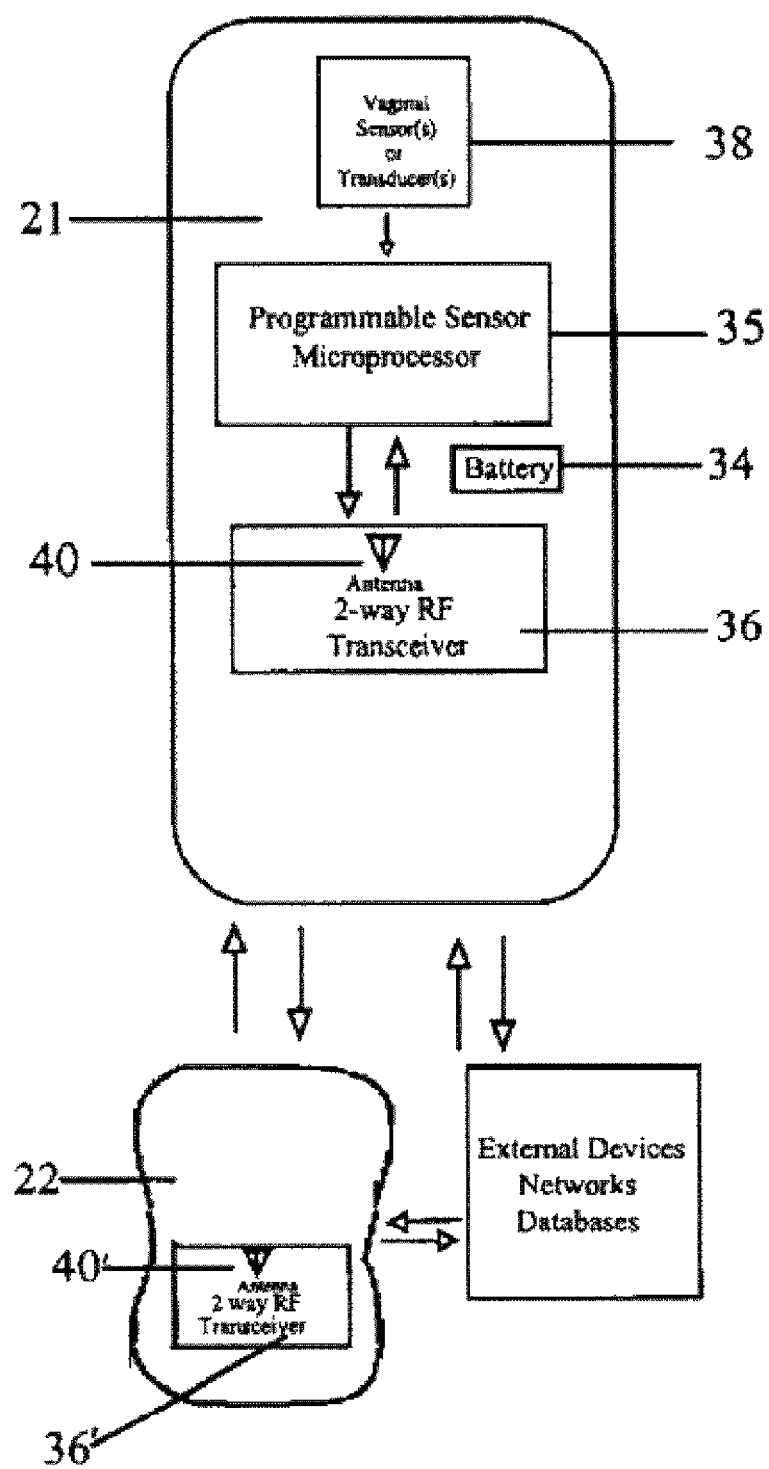
Figure 6:
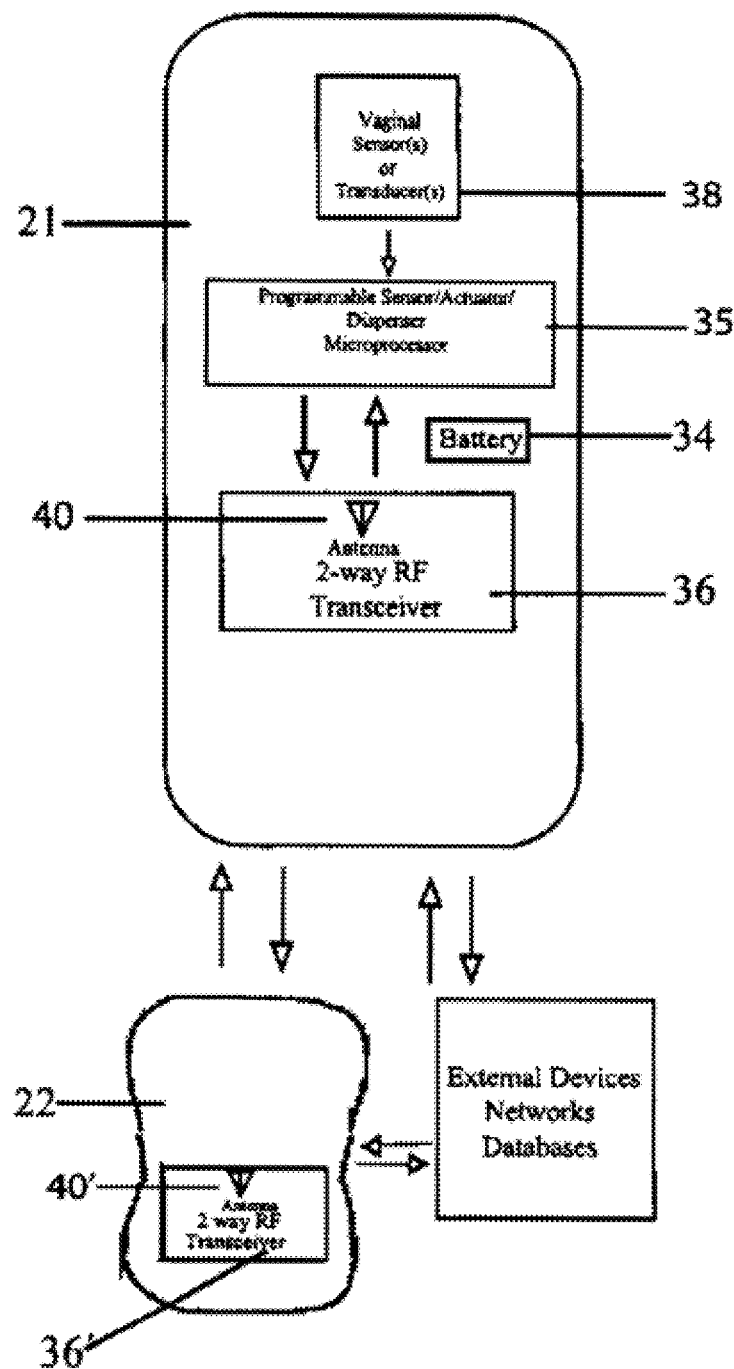

As indicated above, the combination probe and transceiver unit 21 can be provided with means, such as one or more sensors with appropriate circuitry, for transducing vaginal conditions, delivering signals or medication, and/or stimulating perineal musculature and nerves. For this purpose, the combination probe and transceiver 21 is provided with the 2-way wireless communication means 36 for transmitting transduced information to the control unit 22, external devices, networks or databases and for receiving control and programming signals therefrom. Similarly, the control unit or combination controller and transceiver 22 is provided with wireless means, such as a transceiver 36', for sending wireless signals to the unit 21 and for receiving wireless signals therefrom. Thus, a wireless signal feedback loop is provided between the control unit 22 and the probe unit 21. Further inventive embodiments are illustrated in FIGS. 5 and 6.

In particular, the combination controller and transceiver 22 can include means for altering the operational settings of the probe unit 21. The combination probe and transceiver 21 can be provided with sensing or transducing means 38, for example in the form of a muscle contraction sensor, and the unit 21 can also be provided with medication delivery means. In addition, the control unit 22 can be provided with means for altering stimulation signal levels and/or medication delivery signals.

The combination probe and transceiver unit 21 can also be provided with stimulating means (as in the embodiment of FIG. 4), which can be programmed to provide increasing stimulation and/or medication over a given period of time. The stimulating means can include means for automatic adjustment of stimulation levels in response to sensed muscle contractions and/or changes in the vaginal environment. Such stimulating means can be remotely adjustable, for example from the control unit 22 or from another source.

The combination probe and transceiver unit 21 can also be provided with means for sampling cervical fluid, and/or with means for sensing temperature, pH, secretion viscosity, vaginal pathogens and atypical cervical cells. The various sensors and transducers can be provided at any suitable location on the probe as long as the ergonomic character of the probe is maintained. Where appropriate, the sensors/transducers could even be in the form of the electrode rings 26.

As indicated previously, the combination probe and transceiver unit 21 is a sealed unit.

The present invention is, of course, in no way restricted to the specific disclosure of the specification and drawings, but also encompasses any modifications within the scope of the appended claims.

We claim:

1. A system for sensing vaginal conditions or for affecting vaginal or body conditions in a mammal, comprising:
a portable probe unit, said probe unit comprising a substantially cylindrical body having a substantially smooth and substantially sealed outer surface with a rounded end and so dimensioned as to permit comfortable and repeated insertion into, removal from, and containment entirely within a mammal's vagina; means substantially flush with the outer surface of the body of the probe and configured to accomplish at least one of delivering electrical pulses, receiving electrical pulses, sensing or sampling vaginal conditions, and delivering medication; a programmable microprocessor; a memory; a battery; and two-way communication means with antenna and adapted to both transmit signals to a controller unit and receive signals from said controller unit wirelessly and in real time, even when said probe unit is contained entirely within a mammal's vagina; and
the controller unit comprising two-way communication means adapted to both receive signals from said probe unit and transmit signals to said probe unit wirelessly and in real time, even when said probe unit is contained entirely within a mammal's vagina, wherein said signals to said probe unit comprise control and programming signals acting as a feedback loop configured to start, stop, and/or alter the activity of said substantially flush means of said probe unit, either automatically or manually, for sensing vaginal conditions or for affecting vaginal or body conditions.

2. A system according to claim 1, wherein said substantially flush means of said probe unit comprises means for sampling cervical fluid or other changes in the vaginal environment.

3. A system according to claim 1, wherein said substantially flush means of said probe unit comprises means for sensing at least one of temperature, pH, secretion viscosity, vaginal pathogens and atypical cervical cells.

4. A system according to claim 1, wherein said substantially flush means of said probe unit includes at least one of a conductive band and a sensor transducer.

5. A system according to claim 1, wherein said probe unit is adapted to be programmed to start, stop and/or alter at least one of sensing vaginal conditions, sampling vaginal conditions and delivering medication after a predetermined period of time.

6. A system according to claim 1, wherein said probe unit is less than one inch in diameter and less than four inches long.

7. A system according to claim 1, wherein said probe unit is provided with means for facilitating removal from a vagina.

8. A system according to claim 1, wherein said system is adapted to permit a human user to operate said controller unit while said probe unit is in the human user's vagina.

9. A system according to claim 1, wherein said two-way communication means of at least one of said probe unit and said controller unit includes means for transmitting signals to and/or receiving signals from an external device, network and/or database, wirelessly and in real time.

10. A system according to claim 1, wherein at least one of said probe unit and said controller unit include means for holding them together, and wherein means are provided for turning said probe unit on upon separation of said probe unit and said controller unit from one another.

11. A system according to claim 1, wherein said controller unit is adapted to permit manual operation and control of said probe unit.

12. A system according to claim 1, wherein said probe unit is adapted to sense temperature, a physiological marker of a user's fertility cycle, and/or a metabolic abnormality of the user.

13. A system according to claim 1, wherein said substantially flush means of said probe unit is at least one substantially annular electrode.

14. A system according to claim 1, wherein said substantially flush means of said probe unit is adapted to sample cervical fluid.

15. A system according to claim 1, wherein said system is adapted to be programmed to adjust an affecting function thereof in response to a sensed vaginal condition.

16. A system according to claim 1, wherein said two-way communication means of said controller unit includes a transceiver and antenna, and is integrated with a battery, a memory, and a microprocessor.

17. A system according to claim 1, wherein said probe unit contains no surface controls.

18. A system according to claim 1, wherein said controller unit also includes, integrated with a transceiver of said two-way communication means, a programmable microprocessor, battery and antenna.

19. A system according to claim 1, wherein said two-way communication means of said probe unit and of said controller unit are in the form of transceivers.

20. A system according to claim 1, wherein said control signals are adapted to alter medication delivery levels.

* * * * *

(12) INTER PARTES REEXAMINATION CERTIFICATE (555th)

United States Patent
Hochman et al.

(10) Number: US 7,957,794 C1
(45) Certificate Issued: Mar. 12, 2013

(54) SYSTEM AND METHOD FOR TRANSDUCING, SENSING, OR AFFECTING VAGINAL OR BODY CONDITIONS, AND/OR STIMULATING PERINEAL MUSCULATURE AND NERVES USING 2-WAY WIRELESS COMMUNICATIONS

(75) Inventors: Joel S. Hochman, Houston, TX (US); George Sarkis, Orinda, CA (US)

(73) Assignee: Athena Feminine Technologies, Inc., Orinda, CA (US)

Reexamination Request:
No. 95/001,816, Dec. 29, 2011

Reexamination Certificate for:
Patent No.: 7,957,794
Issued: Jun. 7, 2011
Appl. No.: 12/542,511
Filed: Aug. 17, 2009

Related U.S. Application Data

(62) Division of application No. 10/007,393, filed on Oct. 26, 2001, now Pat. No. 7,577,476.

(51) Int. Cl.
  *A61B 5/04* (2006.01)
  *A61B 5/05* (2006.01)
  *A61B 5/00* (2006.01)
  *A61B 5/03* (2006.01)
  *A61B 5/117* (2006.01)
  *A61B 10/00* (2006.01)

(52) U.S. Cl. ........ 600/546; 600/591; 600/551; 600/587; 600/547; 600/549

(58) Field of Classification Search .................. None
  See application file for complete search history.

(56) References Cited

To view the complete listing of prior art documents cited during the proceeding for Reexamination Control Number 95/001,816, please refer to the USPTO's public Patent Application Information Retrieval (PAIR) system under the Display References tab.

*Primary Examiner* — Beverly M. Flanagan

(57) ABSTRACT

A system for sensing vaginal conditions or for affecting vaginal or body conditions in a mammal, The system includes a portable probe unit and a separate controller unit, both of which include two-way communication devices to both transmit signals to, and receive signals from, each other, wirelessly and in real time. The substantially smooth and sealed outer surface of the cylindrical body of the probe unit has a rounded end and is dimensioned to permit comfortable and repeated insertion into removal from, and containment entirely within a mammal's vagina. The probe body has a device substantially flush with its outer surface and configured to deliver electrical pulses, receive electrical pulses, sense or sample vaginal conditions and/or deliver medication. Signals to the probe unit comprise control and programming signals acting as a feedback loop configured to start, stop and/or alter activity of the substantially flush device of the probe unit, either automatically or manually, for sensing vaginal conditions or for affecting vaginal or body conditions.

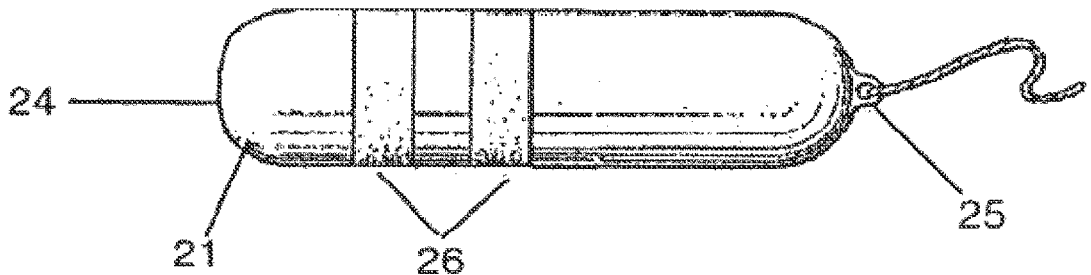

US 7,957,794 C1

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2-20, dependent on an amended claim, are determined to be patentable.

New claims 21-34 are added and determined to be patentable.

1. A system for sensing vaginal conditions or for affecting vaginal or body conditions in a mammal, comprising:
   a portable probe unit, said probe unit comprising a substantially cylindrical body having a substantially smooth and substantially sealed outer surface with a rounded end and so dimensioned as to permit comfortable and repeated insertion into, removal from, and containment entirely within a mammal's vagina;
   means substantially flush with the outer surface of the body of the probe and configured to accomplish at least one of delivering electrical pulses, receiving electrical pulses, sensing or sampling vaginal conditions, and delivering medication;
   a programmable microprocessor;
   a memory;
   a battery; and
   two-way communication means with antenna and adapted to both transmit signals to a controller unit and receive signals from said controller unit wirelessly and in real time, even when said probe unit is contained entirely within a mammal's vagina; and
   the controller unit comprising two-way communication means adapted to both receive signals from said probe unit and transmit signals to said probe unit wirelessly and in real time, even when said probe unit is contained entirely within a mammal's vagina, wherein said signals to said probe unit comprise control and programming signals acting as a feedback loop configured to start, stop, and/or alter the activity of said substantially flush means of said probe unit, either automatically or manually, [for sensing vaginal conditions or] for affecting vaginal or body conditions.

21. *A system for sensing vaginal conditions or for affecting vaginal or body conditions in a mammal, comprising:*
    *a portable probe unit, said probe unit comprising:*
        *a substantially cylindrical plastic body having a substantially smooth and substantially sealed outer surface with a rounded end and so dimensioned as to permit comfortable and repeated insertion into, removal from, and containment entirely within a mammal's vagina;*
        *annular means substantially flush with the outer surface of the plastic body of the probe and configured to accomplish at least one of delivering electrical pulses, sensing or sampling vaginal conditions, and delivering medication;*
        *a programmable microprocessor;*
        *a memory;*
        *a battery; and*
        *two-way communication means with antenna and adapted to both transmit signals to a controller unit and receive signals from said controller unit wirelessly and in real time, even when said probe unit is contained entirely within a mammal's vagina; and*
    *the controller unit comprising two-way communication means adapted to both receive signals from said probe unit and transmit signals to said probe unit wirelessly and in real time, even when said probe unit is contained entirely within a mammal's vagina, wherein said signals to said probe unit comprise control and programming signals acting as a feedback loop configured to start, stop, and/or alter the activity of said substantially flush means of said probe unit, either automatically or manually, for sensing vaginal conditions or for affecting vaginal or body conditions.*

22. *A system according to claim 21, wherein said probe unit is adapted to be preprogrammed to start delivery of electrical pulses from said annular means after a predetermined period of time.*

23. *A system according to claim 21, wherein said probe unit is adapted to be preprogrammed to deliver from said annular means cycles of alternating electrical pulses and rest periods.*

24. *A system according to claim 21, wherein said probe unit is adapted to be preprogrammed to deliver from the annular means electrical pulses of varying stimulation strength.*

25. *A system according to claim 22 wherein said signals to said probe unit override a preprogrammed probe unit.*

26. *A system according to claim 23 wherein said signals to said probe unit override a preprogrammed probe unit.*

27. *A system according to claim 24 wherein said signals to said probe unit override a preprogrammed probe unit.*

28. *A system according to claim 21, further comprising a case for holding said probe unit and said controller unit.*

29. *A system according to claim 28, wherein said probe unit is adapted to turn on automatically upon removal from the case.*

30. *A system according to claim 21, wherein when said probe unit is contained entirely within the vagina, said electrical pulses stimulate musculature and nerves, and said controller unit is adapted to be hand held and operable manually to transmit signals for increasing or decreasing a strength of said electrical pulses.*

31. *A system for sensing vaginal conditions or for affecting vaginal or body conditions in a woman, comprising:*
    *a portable probe unit, said probe unit comprising:*
        *a substantially cylindrical plastic body having a substantially smooth and substantially sealed outer surface with a rounded end and so dimensioned as to permit comfortable and repeated insertion into, removal from, and containment entirely within a woman's vagina;*
        *an electrode ring substantially flush with the outer surface of the plastic body of the probe and configured to accomplish at least one of delivering electrical pulses, and sensing or sampling vaginal conditions;*
        *a programmable microprocessor;*
        *a memory;*
        *a battery; and*
        *two-way communication means with antenna and adapted to both transmit signals to a controller unit* and receive signals from said controller unit wirelessly and in real time, even when said probe unit is contained entirely within a woman's vagina; and the controller unit comprising two-way communication means adapted to both receive signals from said probe unit and transmit signals to said probe unit wirelessly and in real time, even when said probe unit is contained entirely within a woman's vagina, wherein said signals to said probe unit comprise control and programming signals acting as a feedback loop configured to start, stop, and/or alter the activity of said electrode ring of said probe unit, either automatically or manually, for sensing vaginal conditions or for affecting vaginal or body conditions.

32. A system according to claim 31 wherein said controller unit is a hand-held unit comprising an on/off button, whereby with said button said controller unit is operable manually to control said control signals to said probe unit to start the activity of said electrode ring while said probe unit is intravaginally contained.

33. A system according to claim 31 wherein said controller unit is a hand-held unit comprising an on/off button, whereby with said button said controller unit is operable manually to control said control signals to said probe unit to stop the activity of said electrode ring while said probe unit is intravaginally contained.

34. A system according to claim 32 wherein said hand-held controller unit further comprises an increase button or a decrease button, whereby with said increase or decrease button said controller unit is operable manually to control said control signals to said probe unit to increase a stimulating activity of said electrode ring or to decease a stimulating activity of said electrode ring while said probe unit is intravaginally contained.

\* \* \* \* \*